(12) United States Patent
Murray et al.

(10) Patent No.: US 6,548,718 B2
(45) Date of Patent: Apr. 15, 2003

(54) PROCESS FOR CATALYTIC HYDROXYLATION OF, SATURATED OR UNSATURATED, ALIPHATIC COMPOUNDS

(75) Inventors: Brendan Dermot Murray, Houston, TX (US); David Morris Hamilton, Jr., Sugar Land, TX (US)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/841,670

(22) Filed: Apr. 24, 2001

(65) Prior Publication Data

US 2002/0002312 A1 Jan. 3, 2002

Related U.S. Application Data

(63) Continuation-in-part of application No. 09/559,926, filed on Apr. 27, 2000, now abandoned.

(51) Int. Cl.$^7$ .............................................. C07C 27/10
(52) U.S. Cl. ............................... 568/910.5; 568/910
(58) Field of Search .............................. 568/910, 910.5

(56) References Cited

U.S. PATENT DOCUMENTS

| | | | |
|---|---|---|---|
| 4,016,245 A | 4/1977 | Plank et al. | 423/328 |
| 4,251,499 A | 2/1981 | Nanne et al. | 423/329 |
| 4,439,409 A | 3/1984 | Puppe et al. | 423/328 |
| 4,683,217 A | 7/1987 | Lok et al. | 502/214 |
| 4,758,419 A | 7/1988 | Lok et al. | 423/306 |
| 4,795,623 A | 1/1989 | Evans | 423/328 |
| 4,826,667 A | 5/1989 | Zones et al. | 423/277 |
| 4,942,027 A | 7/1990 | Evans | 423/328 |
| 4,954,325 A | 9/1990 | Rubin et al. | 423/328 |
| 5,001,280 A | 3/1991 | Gubelmann et al. | 568/716 |
| 5,055,623 A | 10/1991 | Gubelmann et al. | 568/800 |
| 5,110,995 A | 5/1992 | Kharitonov et al. | 568/800 |
| 5,176,883 A | 1/1993 | Smith, Jr. et al. | 422/211 |
| 5,190,904 A | 3/1993 | Crossland et al. | 502/85 |
| 5,215,725 A | 6/1993 | Sy | 422/212 |
| 5,235,111 A * | 8/1993 | Clerici | |
| 5,236,575 A | 8/1993 | Bennett et al. | 208/46 |
| 5,243,115 A | 9/1993 | Smith, Jr. et al. | 585/446 |
| 5,262,576 A | 11/1993 | Smith, Jr. | 585/447 |
| 5,321,181 A | 6/1994 | Smith, Jr. et al. | 585/467 |
| 5,324,702 A | 6/1994 | Yoo et al. | 502/204 |
| 5,345,006 A | 9/1994 | Smith, Jr. | 568/899 |
| 5,362,697 A | 11/1994 | Fung et al. | 502/71 |
| 5,446,223 A | 8/1995 | Smith, Jr. | 585/313 |
| 5,476,978 A | 12/1995 | Smith, Jr. et al. | 585/323 |
| 5,672,777 A | 9/1997 | Kharitonov | 568/800 |
| 5,756,861 A | 5/1998 | Panov et al. | 568/800 |
| 5,770,782 A | 6/1998 | Knifton et al. | 585/467 |
| 5,808,167 A | 9/1998 | McGhee | 568/716 |
| 5,827,491 A | 10/1998 | Emerson et al. | 423/328.2 |
| 5,866,748 A | 2/1999 | Wittenbrink et al. | 585/734 |
| 5,874,646 A | 2/1999 | Ebner et al. | 568/771 |
| 5,912,391 A | 6/1999 | Barnhart et al. | 568/802 |
| 5,958,370 A | 9/1999 | Zones et al. | 423/706 |
| 6,184,431 B1 | 2/2001 | Slaugh et al. | 585/867 |

FOREIGN PATENT DOCUMENTS

| | | |
|---|---|---|
| EP | 0043562 | 1/1982 |
| EP | 0158976 | 10/1985 |
| WO | WO 99/35087 | 7/1999 |

OTHER PUBLICATIONS

U.S. patent application Ser. No. 09/559,925, Hamilton, filed Apr. 27, 2000.

"A Manganese–Containing Molecular Sieve Catalyst Designed for the Terminal Oxidation of Dodecane in Air," by Robert Raja and John Meurig Thomas, *Chem. Comm.*, 1998, 1841–1842.

Robert A. Meyers, "Handbook of Petroleum Refinery Processes," 2nd Edition, Chapter 10.6, pp. 10.67–10.81 (1996).

"Atlas of Zeolite Structure Types," (published on behalf of the Structure Commission of the International Zeolite Association), by W. M. Meier, D. H. Olson, and Ch. Baerlocher, published by Butterworth–Heinemann, fourth revised edition, 1996.

J. Phys. Chem. 1990, vol. 94, pp. 6425–6430 and pp. 6431–6435.

A.K. Uriarte, et al., 3rd World Conference on Oxidation Catalysis, Graselli, Oyama, Gaffeny, Lyons, Eds., Elsevier Science B.V., 1997, pp. 857–864.

G.I. Panov, et al., Applied Catalysis A: General, 98, 1993, pp. 1–20.

* cited by examiner

*Primary Examiner*—Michael L. Shippen
(74) *Attorney, Agent, or Firm*—Yukiko Iwata

(57) ABSTRACT

A process for hydroxylating aliphatic compounds under catalytic distillation conditions to provide alcohols is provided. The aliphatic compound is contacted, in a distillation column reactor, with an oxidation catalyst and an oxidant under conditions effective to hydroxylate the aliphatic compound while maintaining at least a portion of the aliphatic compound in a liquid phase and separating the hydroxylated product from the un-reacted aliphatic compound in the distillation column reactor.

37 Claims, 1 Drawing Sheet

PROCESS FOR CATALYTIC HYDROXYLATION OF, SATURATED OR UNSATURATED, ALIPHATIC COMPOUNDS

This application is a continuation-in-part of application Ser. No. 09/559,926 filed Apr. 27, 2000, now abandoned, the entire disclosure of which is hereby incorporated by reference.

FIELD OF THE INVENTION

The present invention relates to a process for oxidizing organic compounds using an oxidant over an oxidizing catalyst under catalytic distillation conditions. More particularly, the present invention relates to hydroxylating saturated or unsaturated, aliphatic compounds using an oxidizing gas over a molecular sieve catalyst under catalytic distillation conditions.

BACKGROUND OF THE INVENTION

Various methods are known to produce hydroxylated organic compounds. The majority of such processes require multiple steps to produce a hydroxylated product and many require expensive and/or sensitive catalysts. Direct hydroxylation of organic compounds theoretically should be more cost effective than conventional multi-step processes.

Raja and Thomas, Chem. Commun. 1999, pp. 1841–1842, have reported that dodecane can be partially oxidized with oxygen in an autoclave to produce dodecanol and a variety of oxygenated products. In the reported process, selectivity to dodecanol was about 35%. Because of the existence of a variety of oxygenated products, the separation of the dodecanol from the oxygenated products will be difficult even with an additional separation step.

In addition, the reaction of organics and oxidants can be highly exothermic. Expensive, complex system designs may be required to handle the excess heat. The expense of such reactions is further increased by coke formation from the decomposition products formed at such high temperatures. In addition, the coked catalyst must be regenerated at frequent intervals.

Hydroxylated organic compounds of commercial importance are alcohols of saturated or unsaturated, aliphatic compounds. Alcohols of these compounds are used in making detergents, soaps, surfactants, and freeze point depressants in lubricating oils. These alcohols currently are produced using relatively complex commercial processes, such as by oxo or hydroformylation of long chain olefins. Additional routes to make these alcohols are dehydrohalogenation of alkyl halides.

More economical and efficient processes are needed for directly hydroxylating saturated or unsaturated, aliphatic compounds.

SUMMARY OF THE INVENTION

The present invention provides a process comprising:

continuously contacting, in a distillation column reactor comprising a reaction zone and a distillation zone, at least one, saturated or unsaturated, aliphatic compound having carbon atoms in the range of 6 to 30 with an oxidation catalyst and an oxidant under conditions effective to hydroxylate said aliphatic compound thereby producing a hydroxylated product, while maintaining at least a portion of said aliphatic compound in a liquid phase;

continuously separating said hydroxylated product from the un-reacted aliphatic compound in the distillation zone under conditions effective to vaporize said un-reacted aliphatic compound and maintain said hydroxylated product in a liquid phase; and recovering the said separated hydroxylated product from the distillation column reactor.

DETAILED DESCRIPTION OF THE INVENTION

Figure 1:
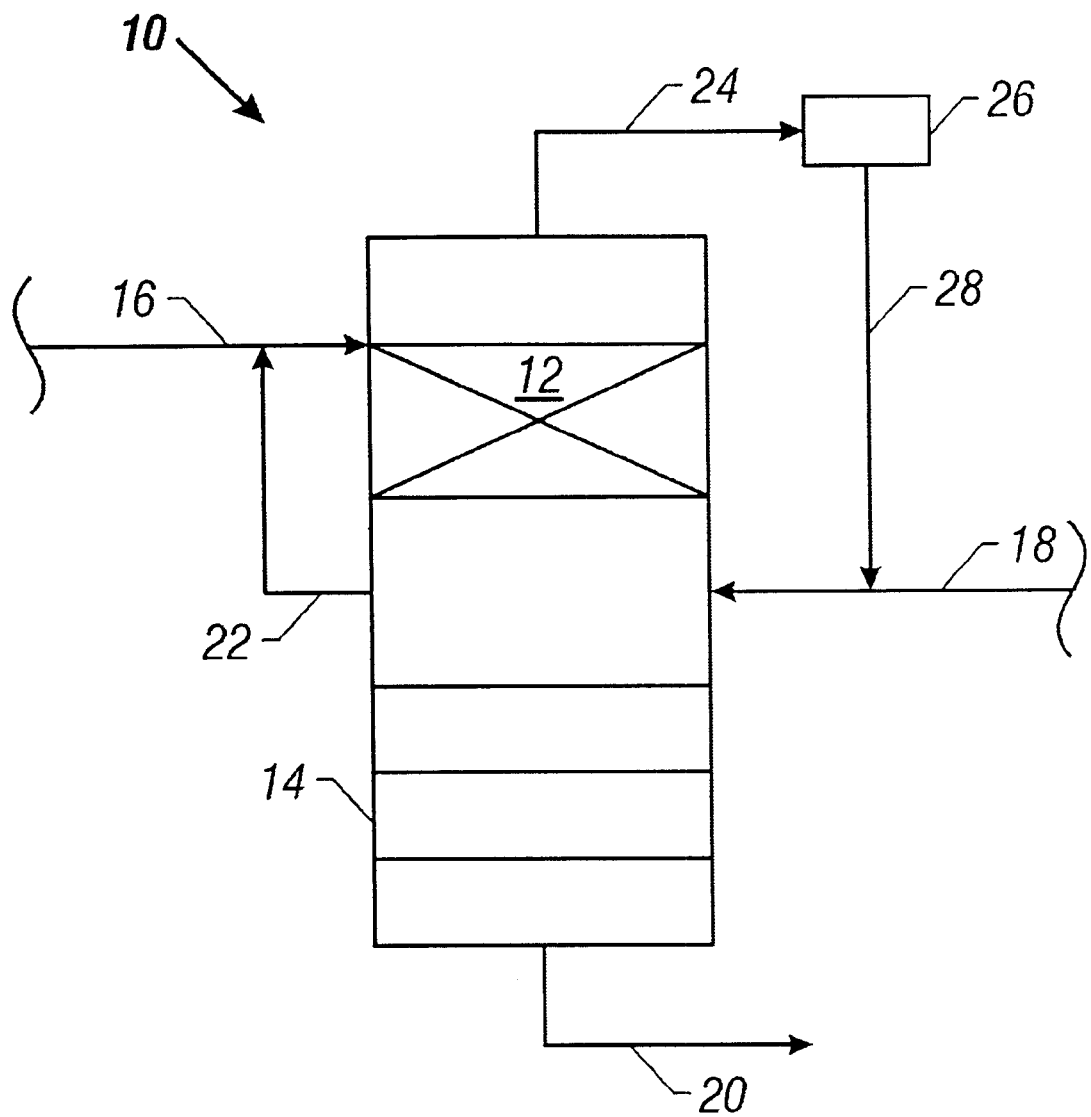
FIG. 1 is a schematic representation of one embodiment of the present invention using a distillation column reactor.

The present invention relates to a process for the direct hydroxylation of saturated or unsaturated, aliphatic compounds ("feedstocks"), particularly, feedstocks containing olefinic and/or paraffinic compounds having average carbon atom numbers in certain ranges, under catalytic distillation conditions. A portion of such feedstock is maintained in a liquid phase. The feedstock is hydroxylated by an oxidant in the presence of an oxidizing catalyst under conditions effective to hydroxylate said saturated or unsaturated, aliphatic compound, and preferably increase the stability and life of the catalyst.

More particularly, the invention relates to a catalytic distillation process for the oxidative hydroxylation of the aliphatic compounds to form the respective hydroxylated derivative at a temperature and a pressure that maintains at least a portion of the aliphatic compound in the liquid phase and manages the heat generated by the exothermic hydroxylation reaction. Reflux of the un-reacted aliphatic compound renders the reaction substantially isothermal. Reduced operating temperatures and heat management maximize the catalyst life by reducing and in some cases preventing catalyst coking.

Suitable, aliphatic compounds can be saturated or unsaturated. The feedstock, aliphatic compounds, typically have average carbon atom numbers in the range of 6 to 30. The aliphatic compounds, for example, can be paraffins, olefins, acetylenes, alicyclics, aldehydes, ketones, and alcohols, optionally substituted with halogens, aromatics, epoxides, nitrites and/or carbonyl groups. Although, the aliphatic compounds can contain aromatic rings, the hydroxylation does not occur at the aromatic ring carbons. Preferred feedstocks include, for example, paraffins and/or olefins having average carbon numbers in the range of 10–18 and alkylbenzenes having average carbon numbers in the range of 16–20. A preferred feedstock may contain, for example, a paraffin that contains a mixture of aliphatic compounds having a major amount of 15 to 18 carbon atoms.

Aliphatic compounds may be obtained from crude oil distillation fractions. Such crude oil distillation fractions may be treated to partially or, more preferably, completely remove sulfur and/or nitrogen containing components. One suitable source of distillation fractions may be paraffin fractions derived from hydrotreated kerosene that may contain a mixture of $C_9$–$C_{18}$ paraffins.

Additional source of aliphatic compounds may be obtained from a paraffinic composition such as obtainable from a Fischer Tropsch process or from an ethylene oligomerisation process (a composition which comprises predominantly linear paraffins). Linear paraffins obtained in a Fischer-Tropsch synthesis are particularly preferred because Fischer-Tropsch products are generally very low in their content of sulfur and nitrogen and they are cost effective. A Fisher-Tropsch process catalytically hydrogenates CO to produce compositions containing aliphatic molecular chains (aliphatic compounds). The Fischer-Tropsch products may or may not comprise oxygenates. The product obtained from the Fischer-Tropsch process may be hydroisomerised, hydrocracked and/or fractionated, for example, by distillation or otherwise, in order to isolate a paraffinic product of the desired composition as the aliphatic compound useful for the process of the invention. Such a hydroisomerisation process and/or subsequent separation are known, for example from U.S. Pat. No. 5,866,748 and U.S. Pat. No. 6,184,431, which are incorporated herein by reference.

Some of the industrial processes useful to produce the aliphatic compounds are described in Robert A Meyers, "Handbook of Petroleum Refinery Processes", $2^{nd}$ Edition, Chapter 10.6, pp. 10.67–10.81 (1996).

Distilled is used herein to mean the compound will vaporize and condense over a defined temperature range at a given pressure. Such that even high molecular weight aliphatic compounds can be hydroxylated using the process of the present invention.

During catalytic distillation, the hydroxylation reaction occurs simultaneously with the distillation, the hydroxylated product being removed from a catalytic zone as it is formed. Removal of the hydroxylated product minimizes side reactions and decomposition of the hydroxylated product. The distillation zone of the reactor is maintained at a temperature and a pressure sufficient to maintain any un-reacted aliphatic compound that travels from the catalytic zone to the distillation zone in the vapor phase, preferably at or above the boiling point of the aliphatic compound at a given pressure. The catalytic zone is maintained at a temperature that is below the boiling point of the hydroxylated product. The un-reacted aliphatic compound eventually reaches a point in the reactor where it boils, and as a result, the temperature of the reactor is controlled by the boiling point of the aliphatic compound at the system pressure. The exothermic heat of the hydroxylation reaction will vaporize a portion of the un-reacted liquid aliphatic compound but will not increase the temperature in the reactor. The hydroxylation reaction has an increased driving force because the hydroxylated product is removed and cannot contribute to a reverse reaction.

In a preferred process, one or more aliphatic compound is hydroxylated under catalytic distillation conditions to form a hydroxylated product having a higher boiling point than the un-reacted aliphatic compound. The hydroxylation reaction is catalyzed by an oxidation catalyst in the presence of an oxidant in a catalytic distillation reactor (distillation column reactor) at conditions that also allow for fractional distillation. The hydroxylation preferably is carried out using a molecular sieve catalyst, preferably a zeolite catalyst, under conditions that maintain at least part of the aliphatic compound in a liquid phase. The catalytic distillation reactor preferably provides both catalytic zones and distillation zones. The "catalytic zone" is defined as the portion of the reactor containing the catalyst where the oxidant and organic react to form hydroxylated product. The "distillation zone," also called the "fractionation zone," is defined as the portion of the reactor adapted to separate the hydroxylated product from the un-reacted aliphatic compound. The distillation zone is a conventional fractionation column design, preferably integral with and downstream of the reaction zone.

The hydroxylated product has a higher boiling point than the oxidant and the un-reacted compound, and is separated from un-reacted organic compound in the distillation zone of the reactor. The temperature along the reactor will vary depending upon the reactants and the products. The highest temperature will be in the bottom of the reactor, in the distillation zone, and the temperature along the column will be the boiling point of the composition at that point in the column under a given pressure. The reactor preferably is operated at a temperature and a pressure effective to vaporize the un-reacted aliphatic compound as it approaches the distillation zone of the reactor while maintaining the hydroxylated product in the liquid phase. The oxidant preferably remains in a gaseous state and un-reacted oxidant is withdrawn as overhead. The hydroxylated product is withdrawn from the distillation zone and any un-reacted compound may be allowed to reflux or it may be withdrawn from the distillation zone and added to the original feed as makeup.

In the catalytic distillation reactor, there exists both a liquid phase, or internal reflux, and a vapor phase. The liquid phase is more dense than a gas phase and allows for a more dense concentration of molecules for reaction over the catalyst. The fractionation or distillation separates hydroxylated product from un-reacted materials, providing the benefits of a combined liquid phase and vapor phase system while avoiding continual contact between the catalyst, the reactants, and the products.

A number of possible catalytic distillation reactor configurations are useful with the present invention, including but not limited to an upflow reactor, a downflow reactor, and a horizontal flow reactor. The reactor contains a reaction or catalytic zone sized to accommodate a fixed catalyst bed and a distillation zone designed to separate the hydroxylated product from un-reacted materials. The distillation zone is integral with the reaction or catalytic zones. Examples of suitable catalytic distillation reactors are found in U.S. Pat. Nos. 5,476,978; 5,262,576; 5,176,883; 5,243,115; 5,321,181; 5,345,006; 5,215,725; 5,770,782; 5,446,223; and 5,190,904, which are hereby incorporated by reference. Specific catalytic distillation column design and process conditions will vary depending upon the reactants used. The design temperature and pressure can be adjusted based on the properties of the reactants including the aliphatic compound and the oxidant, to effectively hydroxylate the aliphatic compound and to separate the hydroxylated product from the reactants based on their respective boiling points at a given pressure.

In a preferred embodiment, the catalytic zone and the distillation zone are in a single column. The catalytic zone contains an amount of catalyst and the distillation zone contains a number of conventional separation trays. The feed(stock) preferably is delivered to the column above the catalyst and the oxidant is fed to the column below the catalyst. Any un-reacted aliphatic compound is either withdrawn from the column once it leaves the catalytic zone, preferably as a vapor, and supplied as makeup or allowed to reflux. The overhead is withdrawn from the column above the catalytic zone and typically will contain a mixture consisting mostly of oxidant and a small amount of un-reacted compound. The oxidant preferably is separated from the un-reacted compound by conventional means and recycled as makeup.

Suitable oxidation catalysts are those that will catalyze the hydroxylation of the aliphatic compound in the presence of an oxidant. Suitable oxidation catalysts include but are not necessarily limited to catalysts comprising molecular sieves (molecular sieve catalysts), including zeolites and non-zeolite materials and mixtures thereof.

The preferred zeolite catalysts contain one or more modified zeolites preferably in the acidic form. These zeolites should contain pore dimensions large enough to admit the entry of the aliphatic compounds. The preferred zeolites include, for example, zeolites of the structural types MFI (e.g., ZSM-5 ), MEL(e.g., ZSM-11), FER (e.g., ferrierite and ZSM-35), FAU (e.g., zeolite Y), BEA (e.g., beta) ,MFS (e.g., ZSM-57), NES (e.g. NU-87), MOR (e.g. mordenite) ,CHA (e.g., chabazite), MTT (e.g., ZSM-23), MWW (e.g., MCM-22 and SSZ-25), EUO (e.g. EU-1, ZSM-50, and TPZ-3), OFF (e.g., offretite), MTW (e.g., ZSM-12) and zeolites ITQ-1, ITQ-2, MCM-56, MCM-49, ZSM-48, SSZ-35, SSZ-39 and zeolites of the mixed crystalline phases such as, for example, zeolite PSH-3. The structural types and references to the synthesis of the various zeolites can be found in the "Atlas of Zeolite Structure Types" (published on behalf of the Structure Commission of the International Zeolite Association), by W. M. Meier, D. H. Olson and Ch. Baerlocher, published by Butterworth-Heinemann, fourth revised edition, 1996. Structural types and references to the zeolites mentioned above are available on the World Wide Web at www.iza-structure.org Such zeolites are commercially available from Zeolyst International, Inc. and Exxon-Mobil Corporation. More preferably, the zeolite is a crystalline alumino-silicate that can contain trace amounts of boron from raw materials without on purpose adding boron sources to enrich boron content.

The zeolite catalyst preferably comprises at least one metal selected from the group consisting of ruthenium, rhodium, iron, magnesium, cobalt, copper, titanium, and iridium, preferably from about 0.01 wt. % to about 5 wt. %, most preferably from about 0.1 wt. % to about 1.5 wt. %. The metal can be incorporated into the catalyst by any means known to those skilled in the art for incorporating metals into zeolites such as, by ion exchange, impregnation, co-mulling, physical admixing or during synthesis of the catalyst. In a preferred embodiment, the zeolite catalyst contains an amount of iron, preferably up to about 5 wt. %, more preferably from about 0.01 wt. % to about 1.5 wt. %. Additional examples of suitable zeolite catalysts can be found in U.S. Pat. Nos. 5,762,777; 5,808,167; 5,110,995; 5,874,646; 4,826,667; 4,439,409; 4,954,325; 5,236,575; 5,362,697; 5,827,491; 5,958,370; 4,016,245; 4,251,499; 4,795,623; 4,942,027 and WO99/35087, which are hereby incorporated by reference.

Non-zeolitic molecular sieves also may be used to catalyze the hydroxylation of organics. Suitable non-zeolitic molecular sieves include but are not necessarily limited to microporous aluminum phosphates (AlPO's) or silica aluminum phosphates (SAPO's) or mixtures thereof containing metals that are capable of being oxidized and reduced, such as, Co, V, Mn, Mg, Cu, Ti, and Fe. These catalysts consist of AlPO's or SAPO's with a fraction of the Al or phosphate ions being replaced during synthesis by a transition metal ion, from about 0.001 wt. % to about 0.6 wt. %, preferably 0.01 wt. % to about 0.4 wt %. A Mn-containing AlPO has been shown to hydroxylate dodecene to dodecanol using air as the oxidant as described in *Chem. Commun.* 1999, pp. 1841–1842, which is incorporated by reference herein. Alternatively, the transition metal may be incorporated into the framework of the catalyst after synthesis of the catalyst using known means including but not necessarily limited to ion exchange, impregnation, co-mulling, and physical admixing. Additional examples of suitable non-zeolitic molecular sieves and their methods of preparation can be found in U.S. Pat. Nos. 4,683,217 and 4,758,419; European patent nos. EP 0 043 562, EP 0 158 976; J. Phys. Chem. 1990, vol. 94, pp. 6425–6464, and pp. 6431–6435.

Another non-zeolite catalyst suitable for use in the present invention includes vanadium-peroxide complexes formed by using hydroquinones to produce peroxide species, which are transferred to the vanadium complexes.

The vanadium-peroxide complexes can be used to hydroxylate organic compounds. A description of this method can be found in U.S. Pat. No. 5,912,391, incorporated by reference herein.

Any suitable oxidant may be used. Examples of oxidant (oxidizing gases) include but are not necessarily limited to, nitrous oxide, oxygen, air, and mixtures thereof. A preferred oxidant for use with zeolite catalysts is nitrous oxide. Regardless of the oxidant used, the molar ratio of oxidant to organic compound is from about 1:1000 to about 100:1, preferably from about 1:1000 to about 10:1, most preferably from about 1:100 to about1:1. In practice, the oxidant to organic compound ratio is the stoichiometric ratio that will yield the desired product and allow safe operation.

The process will be described with reference to paraffins, but the process is not limited to paraffins and may be used with any saturated or unsaturated, aliphatic compound having carbon atoms in the range of 6 to 30. For example, aliphatic compounds having an average carbon atom number in the range of from 8 to 20 (e.g., certain paraffins and/or olefins) can be hydroxylated by the process of the invention to alcohols having carbon atoms in the range of from 8 to 20. Where the product desired is a paraffinic or cycloparaffinic alcohol, the preferred feedstock is a paraffin or a cycloparaffin, respectively. In a more specific example, in the case of $C_{15}$–$C_{18}$ range aliphatic compounds or $C_{10}$–$C_{12}$ range aliphatic compounds, the hydroxylated products will be $C_{15}$–$C_{18}$ range alcohols or $C_{10}$–$C_{12}$ range alcohols, respectively.

In a preferred embodiment, catalytic distillation is carried out in a distillation column reactor at a temperature and pressure effective to hydroxylate the paraffin while fractionating or removing the hydroxylated product, alcohol of the paraffin, from the oxidant and un-reacted paraffin. The temperature in the distillation zone of the reactor is higher than the temperature in the catalytic zone of the reactor. The temperature within the reactor is from about 50° C., preferably from about 125° C., more preferably from about 275° C., to about 450° C., preferably to about 425° C., more preferably to about 390° C. such that the lower boiling components are vaporized and migrate toward the upper portion of the reactor while the higher boiling components migrate toward the lower portion of the reactor. The temperature in the lower portion of the column preferably is higher than the boiling point of paraffin but lower than the boiling point of the alcohol product to achieve an effective separation of the alcohol product from the paraffin.

The pressure in the column is typically in the range from about 0.2 atm to about 50 atm, preferably from about 0.5 atm to about 30 atm. Partial pressure of the feed in the column is in the range of from about 0.01 atm, preferably from 1 atm, more preferably from about 2 atm, to about 40 atm, preferably to about 30 atm, more preferably to about 25 atm. Inert (not reactive to the reactants) gases, such as for example, nitrogen and argon can be used to dilute the reactants to achieve a lower partial pressure of the reactants.

The temperature and pressure can be adjusted within the above referenced ranges by a person skilled in the art, by taking into account the critical temperature and pressure of the feedstock in such a way as to operate the reaction zone below such supercritical temperature and pressure. For example, for a feedstock that contains a major amount, more preferably at least 90 weight percent, of $C_{15}$–$C_{18}$ aliphatic compounds, the hydroxylation reaction is preferably carried out at the reaction zone at a temperature in the range of about 270° C. to about 425° C. and a pressure in the range of about 5 to about 15 atm. In another example, for a feedstock that contains a major amount, more preferably at least 90 weight percent, of $C_{10}$–$C_{12}$ aliphatic compounds, the hydroxylation reaction is preferably carried out at the reaction zone at a temperature in the range of about 175° C. to about 345° C. and a pressure in the range of about 5 to about 15 atm.

The paraffin may be added at any point in the reactor, for example it may be added above or to the fixed bed catalyst or to the reflux as makeup. At least a portion of the paraffin, preferably from about 10% to about 100%, is fed to the reactor in a liquid state. The oxidant preferably is a gas, and is fed to the reactor at a point below the catalyst bed allowing the oxidant to flow upward into the catalyst bed where the oxidant contacts and reacts with the paraffin. Once in the reactor, the paraffin contacts the catalyst and the oxidant, and the paraffin is hydroxylated to form the alcohol product of paraffin. The resulting alcohol has a higher boiling point than paraffin, which allows for easy separation by fractional distillation. In a specific example of hexadecane as the feedstock, hexadecanol has a higher boiling point of 344° C. than hexadecane of 287° C., which allows for easy separation by fractional distillation.

The overhead taken from the distillation column preferably is partially condensed to separate the un-reacted paraffin from the un-reacted oxidant. The partially condensed overheads are passed to an accumulator where paraffin is collected and the gaseous oxidant is taken off. The paraffin and the oxidant can be fed back to the distillation column.

Preferably, heat generated by the hydroxylation reaction is removed from the reactor by the reflux of the un-reacted feedstock, allowing for isothermal operation of the system. Regulating the heat in the reactor also extends the catalyst life.

The process can be used to hydroxylate other aliphatic compounds such as branched olefins to produce branched alcohols that are useful as surfactants. Linear alcohols may be produced by hydroxylating linear olefins in a similar manner.

The zeolite catalyst is believed to catalyze the following reaction, when the feedstock is paraffin and the oxidant is nitrous oxide:

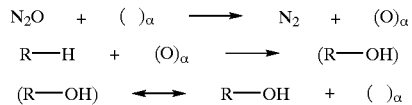

where the formation of the alpha oxygen $(O)_\alpha$ is critical. In the above formula, R—H represents paraffins (e.g., $R=C_nH_{2n+1}$ where n can be in the range of 6 to 30) and R—OH represents the alcohol product of the paraffins. The formation of $(O)_\alpha$ is dependent upon the metal content of the oxidation catalyst (e.g., iron content in the zeolite). The $(O)_\alpha$ will form at low temperatures provided there is sufficient metal present in the oxidation catalyst. Once the $(O)_\alpha$ has formed, desorption of $(O)_\alpha$ as $O_2$ does not occur at temperatures below 300° C. to 330° C., which means that $(O)_\alpha$ can be isolated on the catalyst at moderate temperatures. It is believed that the $(O)_\alpha$ oxygen from the $N_2O$ will remain on the catalyst until it is reacted with the paraffin, thus increasing the amount of $(O)_\alpha$ used to form the alcohol. It has been shown that aliphatics will react with $(O)_\alpha$ at ambient temperatures (e.g. 50° C.) to form alcohols. However, the alcohol formed is bound to the catalyst. It is believed that oxidative hydroxylation under catalytic distillation conditions will prevent the hydroxylated product from binding to the catalyst.

It is believed that the non-zeolite molecular sieves will catalyze the oxidative hydroxylation of the aliphatic compounds in the presence of an oxidant under catalytic distillation conditions. Non-zeolite molecular sieves have been shown to catalyze oxidative hydroxylation reactions of aliphatic compounds similar to those reported for zeolite. In addition, non-zeolite molecular sieves have similar structural and re-dox properties to zeolites.

FIG. 1 illustrates one embodiment of the present invention for the production of a hydroxylated aliphatic or cyclic product. A distillation column reactor 10 has a middle portion that contains a catalyst 12 and a lower portion of the reactor contains a conventional distillation column 14 with a sufficient number of trays to allow for the separation of the hydroxylated product from any un-reacted feed. The feedstock is fed to the reactor through line 16 above the catalyst 12 and the oxidant gas is fed to reactor 10 through line 18 below the catalyst 12. The reaction is exothermic and is initiated by contacting the oxidant and the feedstock in the presence of the catalyst. The hydroxylated products will always have a higher boiling point than the un-reacted feedstock and the oxidant and is recovered from the column via line 20. The temperature in the reactor below the catalyst bed is higher than the boiling point of the feedstock and lower than the boiling point of the hydroxylated product to facilitate the separation of the un-reacted feedstock from the hydroxylated product. Un-reacted feedstock can be withdrawn from the reactor 10 via line 22 and added as makeup to the organic fed through line 16 into the reactor 10. Alternatively, the un-reacted feedstock is allowed to reflux. The oxidant is withdrawn as overhead through line 24 and passed to a condenser 26 to separate any entrained feedstock from the oxidant. The recovered oxidant may then be added as makeup via line 28 to the fresh oxidant feed.

Persons of ordinary skill in the art will recognize that many modifications may be made to the present invention without departing from the spirit and scope of the present invention. The embodiment described herein is meant to be illustrative only and should not be taken as limiting the invention, which is defined in the following claims.

We claim:

1. A process comprising:
   continuously contacting, in a distillation column reactor comprising a reaction zone and a distillation zone, at least one, saturated or unsaturated, aliphatic compound having carbon atoms in the range of 6 to 30 with an oxidation catalyst and an oxidant under conditions effective to hydroxylate said aliphatic compound thereby producing a hydroxylated product, while maintaining at least a portion of said aliphatic compound in a liquid phase;
   continuously separating said hydroxylated product from the un-reacted aliphatic compound in the distillation zone under conditions effective to vaporize said un-reacted aliphatic compound and maintain said hydroxylated product in a liquid phase; and
   recovering the said separated hydroxylated product from the distillation column reactor.

2. The process of claim 1 wherein said separating comprises fractional distillation.

3. The process of claim 1 wherein the oxidant is selected from the group consisting of nitrous oxide, oxygen, air, and mixtures thereof.

4. The process of claim 2 wherein the oxidant is selected from the group consisting of nitrous oxide, oxygen, air, and mixtures thereof.

5. The process of claim 1 wherein the oxidant is nitrous oxide.

6. The process of claim 2 wherein the oxidant is nitrous oxide.

7. The process of claim 1 wherein said conditions comprise a temperature in a range of from about 50° C. to about 450° C.

8. The process of claim 2 wherein said conditions comprise a temperature in a range of from about 50° C. to about 450° C.

9. The process of claim 3 wherein the aliphatic compound is at least one aliphatic compound having carbon atoms in the range of 8 to 20.

10. The process of claim 1 wherein the oxidation catalyst is a molecular sieve catalyst comprising at least one metal selected from the group consisting of ruthenium, rhodium, iridium, iron, magnesium, cobalt, copper, manganese, titanium and vanadium.

11. The process of claim 3 wherein the oxidation catalyst is a molecular sieve catalyst comprising at least one metal selected from the group consisting of ruthenium, rhodium, iridium, iron, magnesium, cobalt, copper, manganese, titanium and vanadium.

12. The process of claim 10 wherein the molecular sieve catalyst comprises an acidified zeolite comprising at least one metal selected from the group consisting of ruthenium, rhodium, iridium, magnesium, titanium, cobalt, copper, and iron.

13. The process of claim 12 wherein the zeolite is selected from the group consisting of zeolite of the structural types MFI, MEL, FER, FAU, BEA ,MFS, NES, MOR,CHA, MTT, MWW, EUO, OFF, MTW and zeolites ITQ-1, ITQ-2, MCM-56, MCM-49, ZSM-48, SSZ-35, SSZ-39, and PSH-3 and mixtures thereof.

14. The process of claim 10 wherein said oxidation catalyst comprises said metal in an amount of from about 0.01 wt % to about 5 wt %.

15. The process of claim 13 wherein said oxidation catalyst comprises said metal in an amount of from about 0.01 wt % to about 5 wt %.

16. The process of claim 15 wherein the zeolite is an alumino-silicate that does not contain additional boron content.

17. The process of claim 10 wherein the molecular sieve catalyst is selected from the group consisting of microporous aluminum phosphates, silica aluminum phosphates, and mixtures thereof comprising at least one metal selected from the group consisting of Co, Cu, V, Mn, Mg, Ti., and Fe.

18. The process of claim 11 wherein the molecular sieve catalyst is selected from the group consisting of microporous aluminum phosphates, silica aluminum phosphates, and mixtures thereof comprising at least one metal selected from the group consisting of Co, Cu, V, Mn, Mg, Ti, and Fe.

19. The process of claim 9 wherein the aliphatic compound is a mixture of aliphatic compounds comprising a major amount of aliphatic compounds having carbon atoms in the range of 15 to 18.

20. The process of claim 1 wherein the aliphatic compound is provided from a stream obtained from a Fischer Tropsch process or from an ethylene oligomerisation process.

21. The process of claim 20 wherein the aliphatic compound is provided from a stream obtained from a Fischer Tropsch process.

22. The process of claim 20 wherein the aliphatic compound is provided from a stream obtained from an ethylene oligomerisation process.

23. The process of claim 7 wherein said conditions comprise a partial pressure of the aliphatic compound from about 0.01 atm to about 40 atm.

24. The process of claim 1 wherein said separating is carried out in a distillation zone under conditions effective to vaporize said un-reacted aliphatic compound and maintain said hydroxylated product in a liquid phase.

25. The process of claim 24 wherein said distillation zone is maintained at a temperature effective to maintain said hydroxylated product in a liquid phase and said un-reacted aliphatic compound in a vapor phase.

26. The process of claim 24 further comprising withdrawing said vaporized un-reacted aliphatic compound and oxidant as overhead.

27. A process comprising
continuously contacting, in a distillation column reactor comprising a reaction zone and a distillation zone, at least one, saturated or unsaturated, aliphatic compound having carbon atoms in the range of 6 to 30 with a molecular sieve catalyst and an oxidant at a temperature in the range of about 50° C. to about 450° C. and a partial pressure of the aliphatic compound in the range of about 0.01 atm to about 40 atm thereby producing a hydroxylated product, while maintaining at least a portion of said aliphatic compound in a liquid phase;
continuously separating said hydroxylated product from the un-reacted aliphatic compound in the distillation zone under conditions effective to vaporize said un-reacted aliphatic compound and maintain said hydroxylated product in a liquid phase; and
recovering the said separated hydroxylated product from the distillation column reactor.

28. The process of claim 27 wherein a liquid phase and a vapor phase are present in said distillation column reactor, further comprising separating said hydroxylated product from said un-reacted aliphatic compound by fractional distillation.

29. The process of claim 27 wherein said oxidant is nitrous oxide.

30. The process of claim 27 wherein said molecular sieve catalyst comprises at least one zeolite comprising from about 0.01 wt % to about 5 wt % of a metal selected from the group consisting of ruthenium, rhodium, iridium, magnesium, cobalt, copper, titanium, and iron.

31. The process of claim 27 wherein said molecular sieve catalyst is selected from the group consisting of microporous aluminum phosphates, silica aluminum phosphates, and mixtures thereof comprising a metal selected from the group consisting of Co, V, Mn, Mg, Cu, Ti, and Fe.

32. The process of claim 27 wherein said molecular sieve catalyst contains from about 0.001 wt. % iron to about 5 wt. % iron based on the catalyst.

33. The process of claim 27 wherein said molecular sieve catalyst contains from about 0.1 wt. % iron to about 1.0 wt. % iron based on the catalyst.

34. The process of claim 27 wherein the aliphatic compound is provided from a stream obtained from Fischer Tropsch process.

35. The process of claim 34 wherein the aliphatic compound is provided from a stream obtained from an ethylene oligomerisation process.

36. The process of claim 34 further comprising withdrawing said vaporized un-reacted aliphatic compounds and oxidant as overhead.

37. The process of claim 1 wherein the aliphatic compound is provided from a stream obtained from a Fischer-Tropsch process further treated in a hydroisomerization and/or hydrocracking process.

* * * * *